United States Patent [19]
Howard et al.

[11] Patent Number: 5,497,626
[45] Date of Patent: *Mar. 12, 1996

[54] OPEN LOOP MIXED REFRIGERANT CYCLE FOR ETHYLENE RECOVERY

[75] Inventors: Lee J. Howard, Allentown; Howard C. Rowles, Center Valley, both of Pa.

[73] Assignee: Air Products and Chemcials, Inc., Allentown, Pa.

[*] Notice: The term of this patent shall not extend beyond the expiration date of Pat. No. 5,377,490.

[21] Appl. No.: 289,862

[22] Filed: Aug. 12, 1994

Related U.S. Application Data

[63] Continuation-in-part of Ser. No. 192,025, Feb. 4, 1994, Pat. No. 5,377,490.

[51] Int. Cl.$^6$ ............................................. F25J 3/06
[52] U.S. Cl. ................................................. 62/23; 62/40
[58] Field of Search .................................. 62/23, 40

[56] References Cited

U.S. PATENT DOCUMENTS

| | | | |
|---|---|---|---|
| 3,675,435 | 7/1972 | Jackson et al. | 62/26 |
| 3,932,156 | 1/1976 | Stern | 62/23 |
| 4,002,042 | 1/1977 | Pryor et al. | 62/28 |
| 4,072,485 | 2/1978 | Becdelievre et al. | 62/23 |
| 4,163,652 | 8/1979 | Gazzi et al. | 62/28 |
| 4,629,484 | 11/1986 | Kister | 62/29 |
| 4,720,293 | 1/1988 | Rowles et al. | 62/24 |
| 4,900,347 | 2/1990 | McCue, Jr. et al. | 62/24 |
| 5,035,732 | 7/1991 | McCue, Jr. | 62/24 |
| 5,157,925 | 10/1992 | Denton | 62/23 |

OTHER PUBLICATIONS

Kaiser, V. et al. "Mixed Refrigerent for Ethylene." *Hydrocarbon Processing* Oct. 1976: 129–31.

*Primary Examiner*—Ronald C. Capossela
*Attorney, Agent, or Firm*—John M. Fernbacher

[57] ABSTRACT

Refrigeration is provided in an ethylene recovery plant by an open-loop mixed refrigeration cycle which utilizes components present in the ethylene-containing feed gas as the mixed refrigerant. Refrigeration is provided by subcooled mixed refrigerant at −175° to −225° F. for the demethanizer overhead condenser and for initial cooling and condensation of the ethylene-containing feed gas. Overall ethylene recoveries of up to 99.9% can be achieved at reduced power consumption compared with conventional ethylene recovery cycles. In addition, significant capital savings can be realized due to the simplification of equipment with the open-loop mixed refrigerant cycle, which can be operated advantageously at pressures between 150 and 400 psia.

27 Claims, 2 Drawing Sheets

OPEN LOOP MIXED REFRIGERANT CYCLE FOR ETHYLENE RECOVERY

This is a Continuation-in-Part of Ser. No. 08/192,025 filed Feb.4, 1994, now U.S. Pat. No. 5,377,490.

FIELD OF THE INVENTION

This invention pertains to the recovery of ethylene from light gases at cryogenic temperatures, and in particular to an open loop mixed refrigerant cycle to provide refrigeration for such recovery.

BACKGROUND OF THE INVENTION

The recovery of ethylene from crude light hydrocarbon gas mixtures is an economically important but highly energy intensive process. Cryogenic separation methods are commonly used which require large amounts of refrigeration at low temperatures, and the development of methods to reduce the power consumption for this refrigeration is of continuing importance in the petrochemical industry.

Ethylene is recovered from light gas mixtures such as cracked gas from hydrocarbon crackers which contain various concentrations of hydrogen, methane, ethane, ethylene, propane, propylene, and minor amounts of higher hydrocarbons, nitrogen, and other trace components. Refrigeration for condensing and fractionating such mixtures is commonly provided at successively lower temperature levels by ambient cooling water, closed cycle propylene and ethylene systems, and work expansion or Joule-Thomson expansion of pressurized light gases produced in the separation process. Numerous designs have been developed over the years using these types of refrigeration as characterized in representative U.S. Pat. Nos. 3,675,435, 4,002,042, 4,163,652, 4,629,484, 4,900,347, and 5,035,732.

The use of mixed refrigerant systems can be integrated with one or more of the above-mentioned refrigeration methods to improve the overall energy efficiency of ethylene recovery. Mixed refrigerants for such systems typically comprise methane, ethane, ethylene, propane, propylene, and optionally other light components. Mixed refrigerants exhibit the desirable property of condensing over a range of temperatures, which allows the design of heat exchange systems which are thermodynamically more efficient than single refrigerant systems.

U.S. Pat. No. 4,072,485 describes a closed-loop mixed refrigerant cycle for providing low level refrigeration in a natural gas processing plant, or in the cryogenic section of an ethylene plant which utilizes one or more partial condensation zones to cool feed gas. In this cycle, the mixed refrigerant is half condensed with cooling water or air at near ambient temperature and then totally condensed at +50° F. and subcooled to about −25° F. with several levels of propane or propylene refrigeration. In ethylene plant service, the mixed refrigerant is then utilized to provide refrigeration over the temperature range of −40° F. to −148° F., i.e., it is confined to the same temperature range as the ethylene refrigeration it replaces. A more specific example of this cycle of ethylene plant service is described in an article by Victor Kaiser, et al., "Mixed Refrigerant for Ethylene", in the October 1976 issue of *Hydrocarbon Processing*, pages 129–131.

U.S. Pat. No. 4,720,293 describes a process for recovering ethylene from refinery off-gas which utilizes a closed-loop mixed refrigerant cycle. In this process, the mixed refrigerant is utilized in a single heat exchanger to provide refrigeration over a relatively warm temperature range of +60° F. to −85° F. Refrigeration at lower temperature levels is supplied by vaporization of separated ethane at low partial pressure and high total pressure, and by work expansion of light gases which are typically rejected to fuel along with the ethane.

With the conventional process technology described above, the feed gas chilling and demethanizing must be carried out at pressures in the range of 450 to 650 psia in order to achieve high ethylene recovery (99% or more) because the propylene/ethylene cascade system can provide refrigeration no colder than −150° F. for feed gas chilling and for demethanizer column condenser refrigeration. The amount of refrigeration for feed cooling below −150° F. which can be produced from other process streams in an ethylene plant is limited by operating constraints such as the amount of high pressure hydrogen recovered and the fuel system pressure(s). These constraints limit the amount of expander refrigeration which can be produced, which in turn limits the ethylene recovery. Pressures between 450 and 650 psia are required in the feed gas chilling train and in the demethanizer column so that most of the ethylene can be condensed above −150° F., and so that sufficient fuel gas expansion refrigeration at colder temperatures is available to condense most of the remaining ethylene and achieve low ethylene loss in the demethanizer column overhead vapor.

The integration of improved mixed refrigerant cycles with conventional intermediate and low temperature refrigeration holds promise for further reduction of energy consumption in ethylene recovery. In particular, it is desirable to improve the efficiency of refrigeration at the lowest temperature levels required for high ethylene recovery. The invention described in the following specification and defined in the appended claims provides a unique open loop mixed refrigeration cycle for efficient ethylene recovery.

SUMMARY OF THE INVENTION

The present invention as illustrated in the accompanying drawings is a refrigeration method for the recovery of ethylene in which an ethylene-containing mixed gas stream comprising hydrogen, methane, ethane, and ethylene is cooled in a cold feed condensing zone (101) to yield at least one cold feed condensate (5) and a light gas stream (3). The cold feed condensate (5) is subcooled by indirect heat exchange in a mixed refrigerant cooling zone (107) with one or more cold process streams to yield a subcooled condensate (11). A first portion (13) of the subcooled condensate (11) is flashed and the resulting flashed stream (15) provides overhead condenser refrigeration for at least one of the demethanizer columns by indirect heat exchange, which warms and at least partially vaporizes the resulting flashed stream (15) to yield a demethanizer overhead condenser refrigerant outlet stream (17). A second portion (19) of the Subcooled condensate (11) is flashed to provide at least a portion of the refrigeration required to cool the ethylene-containing mixed gas stream and to condense a portion thereof by indirect heat exchange in the cold feed condensing zone (101), which warms and at least partially vaporizes the second portion (19) of subcooled condensate to yield a cold feed condensing zone refrigerant outlet stream (9).

The ethylene-containing mixed gas stream typically contains ethylene, hydrogen, and $C_1$ to $C_3$ hydrocarbons. The cold feed condensing zone (101) comprises at least one dephlegmator, or at least one partial condenser, or a combination thereof.

Optionally, a third portion (21) of the subcooled condensate (11) is flashed and used to provide at least a portion of the refrigeration required to subcool the cold feed condensate (5) by indirect heat exchange in the mixed refrigerant cooling zone (107), which warms and at least partially vaporizes the resulting flashed subcooled condensate (23). Cooling in the mixed refrigerant cooling zone (107) preferably is provided by work expanding at least a portion of the light overhead product from the one or more demethanizer columns. Further cooling optionally is provided by a hydrogen-rich vapor stream and one or more methane-rich streams which are obtained by further cooling and partially condensing at least a portion of the light gas stream (3).

Open loop refrigeration is provided for the demethanizer overhead condenser (111) and the feed cooling and condensing steps by compressing one or more mixed refrigerant vapor streams in a mixed refrigerant compression zone (117) and cooling the resulting compressed stream to yield a partially condensed mixed refrigerant stream (33), and further condensing the stream by indirect heat exchange with one or more additional cold process streams in the mixed refrigerant cooling zone (107). A first portion (39) of the resulting further condensed mixed refrigerant (35) is combined with the cold feed condensate (5) from the cold feed condensing zone (101). A second portion (41) of the further condensed mixed refrigerant (35) is flashed, warmed in mixed refrigerant cooling zone 107 to provide refrigeration, and is thereby vaporized to yield a mixed refrigerant cooling zone second outlet vapor (43). A third portion (37) of said further condensed mixed refrigerant (35) is withdrawn for ethylene product recovery.

Low pressure inlet refrigerant for the mixed refrigerant compression zone (117) is provided by the cold feed condensing zone refrigerant outlet stream (9) and optionally by the mixed refrigerant cooling zone first outlet vapor (18). Intermediate pressure inlet refrigerant for the mixed refrigerant compression zone (117) is provided by the mixed refrigerant cooling zone second outlet vapor (43) and optionally by the mixed refrigerant cooling zone first outlet vapor (18).

In an alternative embodiment, the ethylene-containing mixed gas feed stream (51) to the cold feed condensing zone (101) is provided optionally by cooling the feed gas mixture (1) and condensing a portion thereof in a warm feed condensing zone (125) to yield the ethylene-containing mixed gas feed stream (51) and a warm feed condensate (49). The warm feed condensing zone (125) comprises at least one dephlegmator, or at least one partial condenser, or a combination thereof. The warm feed condensate (49) is flashed to provide at least a portion of the refrigeration for the cooling and condensing of the feed gas mixture (1) by indirect heat exchange with the resulting flashed warm feed condensate (50), thereby vaporizing the flashed feed condensate to yield a warm feed condensing zone refrigerant vapor (53). Additional intermediate pressure inlet refrigerant is provided to the mixed refrigerant compression zone (117) by the warm feed condensing zone refrigerant vapor (53).

Optionally, at least a portion (20) of the demethanizer overhead condenser refrigerant outlet stream (17) is combined with the resulting flashed warm feed condensate (50) to provide additional refrigeration to the warm feed condensing zone (125).

A key feature of the present invention is that the feed chilling train, open loop refrigeration cycle, and downstream equipment for separation of the condensed feed liquids can be operated in the pressure range of 150 to 400 psia, thereby achieving satisfactory ethylene recovery with lower refrigeration requirements and lower capital costs in the downstream separation equipment compared with operation at conventional pressures in the range of 450 to 600 psia.

The present invention thus utilizes an efficient mixed refrigerant system for ethylene feed condensation in which the system operates in an open loop mode wherein the mixed refrigerant is provided by components in the ethylene-containing feed gas.

DETAILED DESCRIPTION OF THE INVENTION

Figure 1:
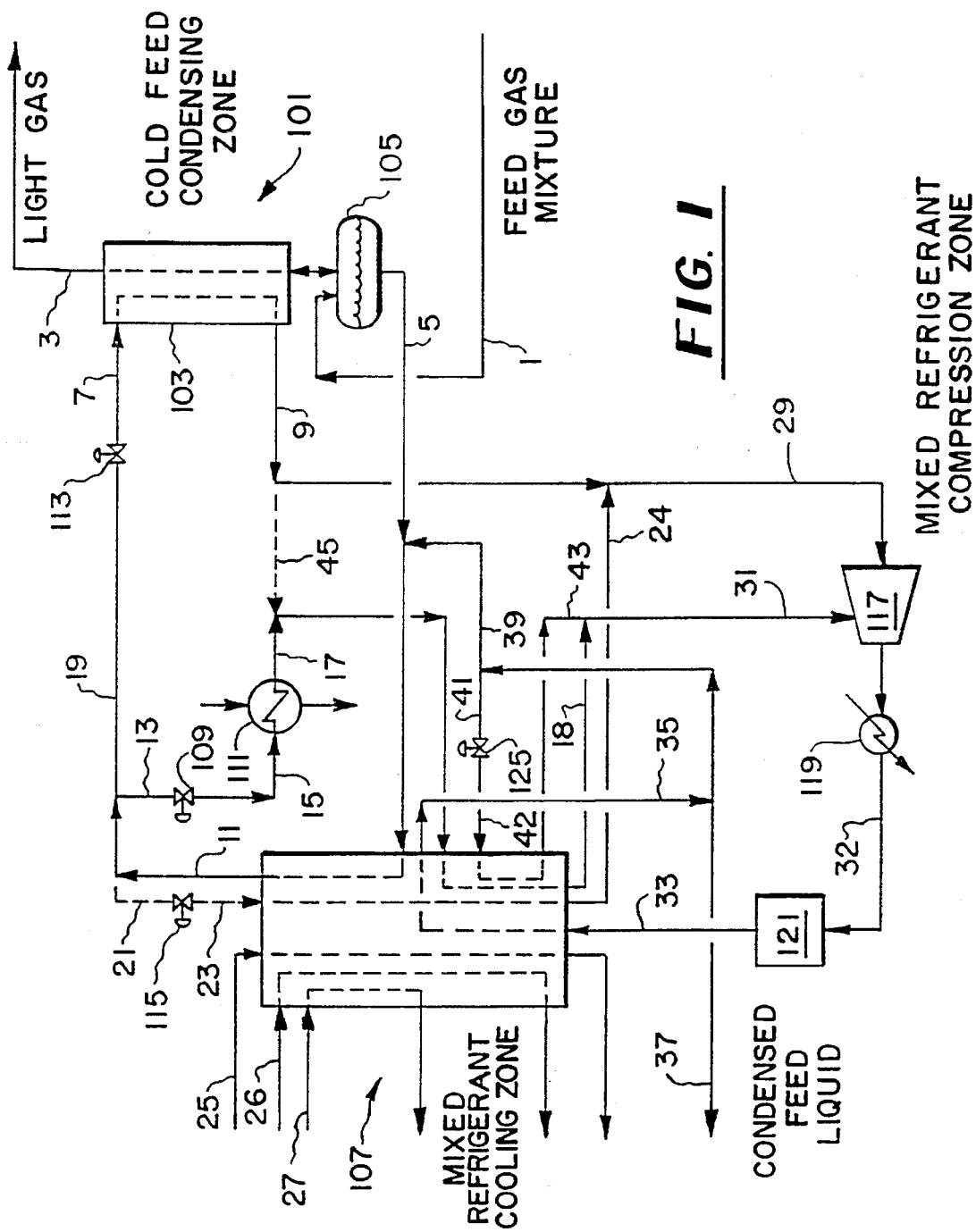
FIG. 1 is a schematic flow diagram of the present invention which utilizes an open loop mixed refrigerant with one feed cooling and condensation zone.

Essentially all ethylene plants, and some ethylene recovery processes, use an ethylene-propylene cascade refrigeration system to provide the predominant amount of refrigeration required in the ethylene plant. Most of the propylene (high level) refrigeration is utilized at several pressure/temperature levels in the initial feed precooling and fractionation sections of the plant, to cool the feed gas from ambient temperature to about −35° F. and to condense the ethylene refrigerant at about −30° F. Similarly, the ethylene (low level) refrigeration is utilized at several pressure/temperature levels in the cryogenic section of the plant to cool the feed from −35° F. to about −145° F. in order to condense the bulk of the ethylene in the form of liquid feeds to one or more demethanizer columns, and is used in at least one of the demethanizer column overhead condenser(s) at about −100° F. to −235° F. to provide reflux to the column(s). Ethylene is normally not used to provide refrigeration below −150° F. since that would result in sub-atmospheric pressure at the suction of the ethylene compressor. Refrigeration below −150° F. to condense the remaining ethylene from the feed gas is provided primarily by work expansion of hydrogen- and methane-containing light gas streams and/or by vaporization of methane refrigerant which has been condensed by ethylene refrigerant. The work expanded gases are normally used as fuel and consist primarily of the overhead vapor from the demethanizer column, mostly methane, and any uncondensed feed gas, mostly $H_2$ and methane, which is not processed in a $H_2$ recovery section of the ethylene plant or ethylene recovery process. Refrigeration also may be recovered from one or more of the hydrogen-rich and methane-rich streams produced in a hydrogen recovery section.

Cooling and condensation of the feed gas preferably is accomplished by dephlegmation in a dephlegmator, which is a rectifying heat exchanger which partially condenses and rectifies the feed gas. Typically a dephlegmator yields a degree of separation equivalent to multiple separation stages, typically 5 to 15 stages. Alternatively, cooling and condensation of the feed gas is accomplished in a conventional condenser, defined herein as a partial condenser, in which a feed gas is partially condensed to yield a vapor-liquid mixture which is separated into vapor and liquid streams in a simple separator vessel. A single stage of separation is realized in a partial condenser.

With the conventional process technology described above, the feed gas chilling and demethanizing must be carried out at pressures in the range of 450 to 650 psia in order to achieve high ethylene recovery (99% or more) because the propylene/ethylene cascade system can provide refrigeration no colder than −150° F. for feed gas chilling and for demethanizer column condenser refrigeration. The amount of refrigeration for feed cooling below −150° F. which can be produced from other process streams in an ethylene plant is limited by operating constraints such as the amount of high pressure hydrogen recovered and the fuel system pressure(s). These constraints limit the amount of expander refrigeration which can be produced, which in turn limits the ethylene recovery. Pressures between 450 and 650 psia are required in the feed gas chilling train and in the demethanizer column so that most of the ethylene can be condensed above −150° F., and so that sufficient fuel gas expansion refrigeration at colder temperatures is available to condense most of the remaining ethylene and achieve low ethylene loss in the demethanizer column overhead vapor.

The present invention comprises an open-loop mixed refrigerant cycle designed to provide the refrigeration required for cooling ethylene plant or other ethylene recovery process feed gas in the range of about −20° F. to −220° F. Feed gas is cooled and condensed in part in one or more feed cooling/condensing zones and preferably at least one of the cooling/condensing zones is a dephlegmator. Alternatively, at least one of the cooling/condensing zones is a partial condenser. Alternatively, a combination of one or more dephlegmators and partial condensers can be used in the cooling/condensing zones. In an embodiment having two cooling/condensing zones, liquid condensed in a warmer cooling/condensing zone, e.g., a partial condenser, is optionally subcooled, flashed to an intermediate pressure (50 to 250 psia), vaporized and warmed to provide the warm level refrigeration required for the process. Liquid condensed in the cold cooling/condensing zone, e.g., a dephlegmator, is optionally subcooled, flashed to low pressure (15 to 50 psia), vaporized and warmed to provide the cold level refrigeration required for the process. One or more intermediate level feed cooling/condensing zones can be added to produce additional condensed feed liquid streams to be vaporized and warmed (at additional pressure levels, if desirable) to provide intermediate level refrigeration for the process. Any of these condensed feed liquid streams can be supplemented as necessary with additional mixed refrigerant from the open-loop cycle to increase the amount of refrigeration available for any feed or mixed refrigerant cooling/condensing zone or to increase the amount of refrigeration available for a demethanizer condenser. Refrigeration for one or more demethanizer column condensers may be supplied by any of the condensed feed liquid streams in series and/or in parallel with any of the feed cooling/condensing zones or mixed refrigerant cooling/condensing zones. All of the liquids condensed from the feed gas are ultimately removed from the open-loop cycle to recover an ethylene product and are normally separated in a fractionation unit, typically after first being processed in one or more demethanizer columns to remove methane and other light gases.

The cooling, condensation, and open loop refrigeration steps can be operated advantageously in the range of 150 to 400 psia, and the feed gas mixture can be provided at a pressure of 150 to 400 psia. Cooling and condensation of the feed gas preferably is accomplished by dephlegmation in a dephlegmator, which is a rectifying heat exchanger which partially condenses and rectifies the feed gas. Typically a dephlegmator yields a degree of separation equivalent to multiple separation stages, typically 5 to 15 stages. Alternatively, cooling and condensation of the feed gas is accomplished in a conventional condenser, defined herein as a partial condenser, in which a feed gas is partially condensed to yield a vapor-liquid mixture which is separated into vapor and liquid streams in a simple separator vessel. A single stage of separation is realized in a partial condenser.

A first embodiment of the invention is described in detail by the schematic flowsheet of FIG. 1. Feed gas mixture 1, obtained for example by initial cooling and separation of cracked gases from a hydrocarbon cracking unit, is typically at −20° F. to −80° F. and 200 to 550 psia, but can be provided in the range of 150 to 400 psia. The feed gas typically contains hydrogen, methane, ethane, ethylene, propane, propylene, and other minor components at low concentrations. The actual composition will depend on the hydrocarbon cracking feedstock and degree of pretreatment; typical composition ranges are 5 to 40 mole % hydrogen, 5 to 40 mole % methane, 5 to 40% ethylene, 5 to 30 mole % ethane, lower concentrations of propane, propylene, and heavier hydrocarbons, and lower concentrations of nitrogen and carbon monoxide. Feed gas mixture 1 is cooled and condensed in part in cold feed condensing zone 101, preferably utilizing a dephlegmator, to yield light gas 3 comprising chiefly hydrogen and methane and feed condensate 5 enriched in $C_2$ and heavier hydrocarbons. Zone 101 is shown as dephlegmator 103 and liquid accumulator 105. Refrigerant stream 7, described later, provides refrigeration at −180° to −235° F. by indirect heat exchange in dephlegmator 103 and is at least partially vaporized to yield cold feed condensing zone refrigerant outlet stream 9. In cold feed condensing zone 101, dephlegmator 103 rectifies feed gas mixture 1 in an equivalent 5 to 15 stages of separation which reduces ethylene losses in light gas stream 3 and reduces the light component content (mostly methane) of feed condensate 5, thereby increasing overall ethylene recovery and purity. Feed condensate 5 at about −25° F. to −100° F. is subcooled in mixed refrigerant cooling zone 107 by indirect heat exchange with cold streams defined later to yield subcooled condensate 11 at about −175° to −225° F. Alternatively, cold feed condensing zone 101 is a single-stage partial condenser.

A first portion 13 of subcooled condensate 11 is flashed to 15 to 250 psia across pressure reducing valve 109 to provide refrigerant as resulting flashed stream 15 at about −100° F. to −235° F. to demethanizer column overhead condenser 111, yielding at least partially vaporized demethanizer overhead condenser refrigerant outlet stream 17. A second portion 19 of subcooled condensate 11 is flashed to 15 to 50 psia across pressure reducing valve 113 to provide refrigerant stream 7 at −180° to −235° F. to dephlegmator 103. Optionally, a third portion 21 of subcooled condensate 11 is flashed to 15 to 50 psia across pressure reducing valve 115 to provide flashed subcooled condensate 23 as a refrigerant at −180° to −235° F. to mixed refrigerant cooling zone 107. Additional refrigeration is provided to mixed refrigerant cooling zone 107 by cold process streams 25, 26, and 27, typically available at −175° to −235° F., which supply the major portion of the refrigeration to mixed refrigerant cooling zone 107. These cold streams, which are produced in other sections of the ethylene plant (not shown), may include work-expanded light gas overhead from a demethanizer column, work-expanded light gas separated from the feed gas, as well as cold methane and hydrogen streams from a hydrogen recovery section of the plant. The flow rate of flashed subcooled condensate 23 is controlled to balance the total amount of refrigeration required to subcool the high pressure mixed refrigerant, and to compensate for variations in the properties of cold process streams 25, 26, and 27. Additional cold process streams (not shown) can be used to supplement refrigeration from the described cold process streams 25, 26, and 27. Typically about 60 to 100% of the total refrigeration for mixed refrigerant cooling zone 107 is provided by cold process streams 25, 26, and 27; the remainder is provided by flashed subcooled refrigerant 23 and supplemental flashed refrigerant, stream 42.

Mixed refrigerant cooling zone 107 comprises one or more conventional type cooling and condensing heat exchangers.

The remainder of the refrigeration cycle in this embodiment of the invention comprises an open-loop mixed refrigerant system driven by mixed refrigerant compression zone 117 which compresses one or more refrigerant vapor streams comprising methane, ethane, ethylene, and heavier hydrocarbons condensed from the feed gas. Mixed refrigerant compression zone 117 comprises a single-stage or preferably multi-stage compressor of the axial or centrifugal type. Preferably the compressor is a multi-stage type which Operates with multiple inlet streams, typically with a low pressure vapor stream introduced into the first stage and an intermediate pressure vapor stream introduced at an interstage location. Low pressure mixed refrigerant vapor 29 at 15 to 50 psia and optionally intermediate pressure mixed refrigerant vapor 31 at 50 to 250 psia are compressed to 200 to 550 psia, or alternatively to 150 to 400 psia, cooled in cooling water exchanger 119 to yield cooled compressed refrigerant 32, and further cooled and partially condensed in propane or propylene refrigeration system 121. The resulting partially condensed mixed refrigerant stream 33, now at about −20° F. to −50° F., is further cooled and condensed in mixed refrigerant cooling zone 107 to yield mixed refrigerant 35 at about −50° F. to −125° F.

Refrigeration for condensing mixed refrigerant stream 33 is provided in part by warming partially vaporized demethanizer overhead condenser refrigerant outlet stream 17 in mixed refrigerant cooling zone 107 to yield mixed refrigerant cooling zone first outlet vapor 18. Additional refrigeration is provided by cold process streams earlier defined.

A portion 37 of mixed refrigerant 35, equivalent in flow to feed condensate 5, is withdrawn for recovery of ethylene product and further purification in the fractionation section of the plant. Another portion 39 optionally is combined with feed condensate 5 to provide additional refrigerant for cold feed condensing zone 101 and demethanizer overhead condenser 111. A third portion 41 is flashed optionally to 50 to 250 psia across pressure reducing valve 125 to provide additional refrigeration to mixed refrigerant cooling zone 107. Vaporization of flashed portion 42 yields mixed refrigerant cooling zone second outlet vapor 43 which provides at least a portion of intermediate pressure mixed refrigerant vapor 31 to mixed refrigerant compression zone 117.

Optionally, refrigerant 23 is warmed in mixed refrigerant cooling zone 107 to provide additional refrigeration thereby yielding vaporized mixed refrigerant 24. Vaporized mixed refrigerant 24 is combined with cold feed condensing zone refrigerant outlet stream 9 to provide low pressure mixed refrigerant vapor 29 to mixed refrigerant compression zone 117. When subcooled condensate 13 is flashed across pressure reducing valve 109 to an intermediate pressure of 50 to 250 psia, mixed refrigerant cooling zone first outlet vapor 18 is combined with mixed refrigerant cooling zone second outlet vapor 43 to provide intermediate pressure mixed refrigerant vapor 31 to mixed refrigerant compression zone 117, When subcooled condensate 13 is flashed across pressure reducing valve 109 to a low pressure of 15 to 50 psia, mixed refrigerant cooling zone first outlet vapor 18 is combined (not shown) with cold feed condensing zone refrigerant outlet stream 9 to provide low pressure mixed refrigerant feed 29 to mixed refrigerant compression zone 117.

Optionally, at least a portion 45 of cold feed condensing zone refrigerant outlet stream 9 may be combined with partially vaporized demethanizer condenser refrigerant outlet stream 17 to provide additional refrigeration to mixed refrigerant cooling zone 107. This option is preferred if outlet stream 9 is only partially vaporized. An alternative embodiment of the invention is given in FIG. 2 in which the cold feed condensing zone 101 is preceded by warm feed condensing zone 125. Feed gas mixture 1 is typically at −20° F. to −80° F. and 200 to 550 psia, but can be provided in the range of 150 to 400 psia. Feed gas mixture 1 is initially cooled to −50° F. to −125° F. and is partially condensed in warm feed condensing zone 125, which may be a partial condenser consisting of cooling exchanger 127 and separator 129. Partially condensed feed 47 is separated into warm feed condensate 49 and ethylene-containing mixed gas stream 51. Stream 51 provides the feed to cold feed condensing zone 101, which preferably is dephlegmator 103 as described in the first embodiment of the invention given in FIG. 1. Warm feed condensate 49 is flashed to 50 to 250 psia across pressure reducing valve 131 to yield flashed warm feed condensate 50 which provides at least a portion of the refrigeration needed to cool feed gas mixture 1 by indirect heat exchange in warm feed condensing zone 125. Vaporized refrigerant stream 53 provides additional intermediate pressure mixed refrigerant vapor 31 to mixed refrigerant compression zone 117.

Optionally, additional refrigeration for warm feed condensing zone 125 is provided by flashing another portion 55 of mixed refrigerant liquid 35 across pressure reducing valve 133 and combining the flashed refrigerant with flashed feed condensate 50 downstream of pressure reducing valve 131. Optionally, additional refrigeration for warm feed condensing zone 125 is provided by combining at least a portion 20 of partially vaporized demethanizer overhead condenser refrigerant outlet stream 17 with flashed feed condensate 50. The remaining portion of the mixed refrigerant cycle of FIG. 2 is essentially the same as in the corresponding portion of FIG. 1.

Subcooling of mixed refrigerant liquid 11 to about −175° F. to −225° F. in the present invention is highly advantageous in ethylene plants in order to provide sufficiently cold refrigeration to cool the feed gas to −170° F. to −220° F., which is the temperature range required for high (99+%) or ultra-high (99.75+%) ethylene recovery. To attain these high ethylene recoveries, feed gas must typically be cooled to −190° F. to −220° F. in ethylene plants utilizing conventional partial condensers, or −170° F. to −190° F. in ethylene plants utilizing dephlegmators.

Figure 2:
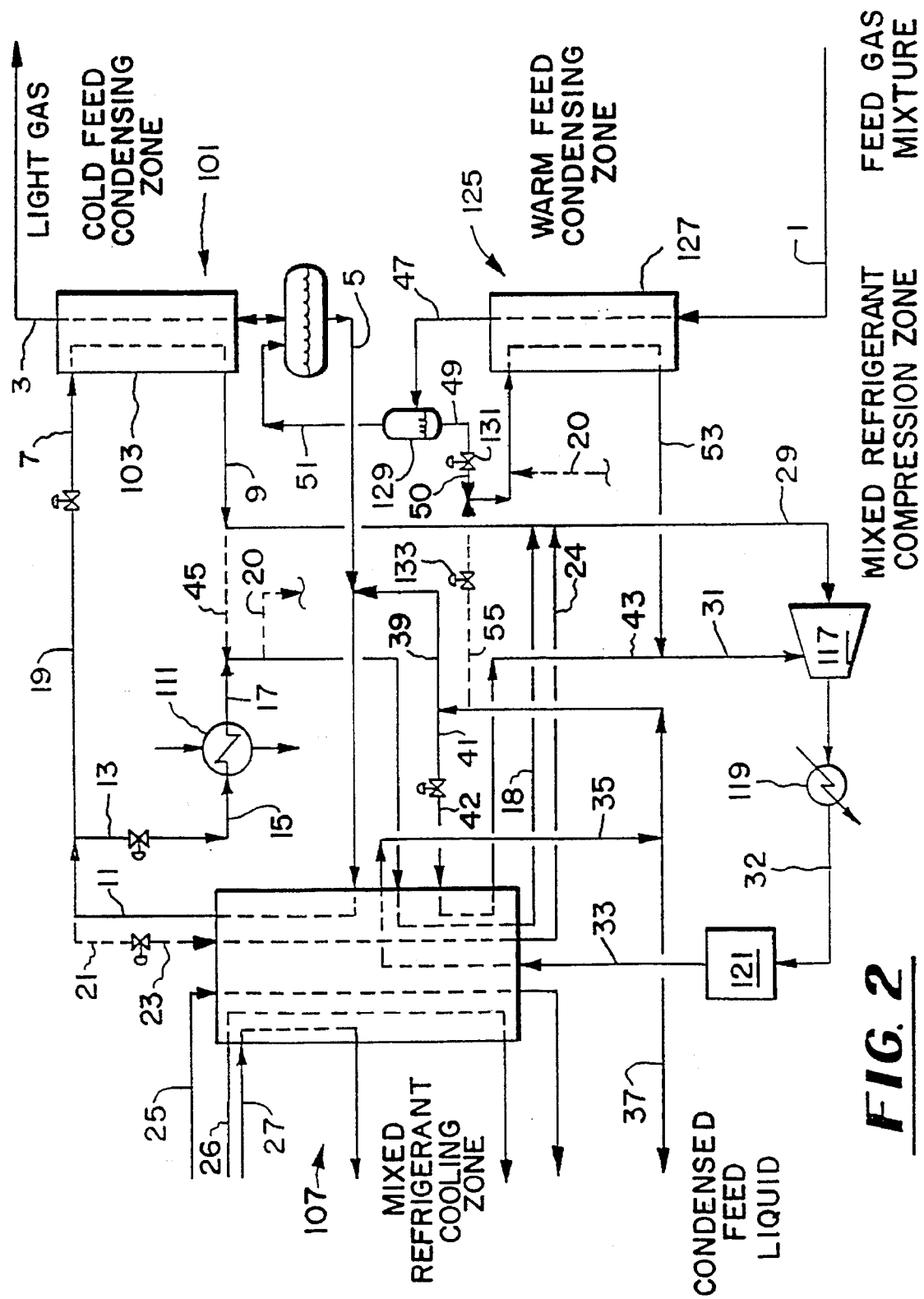
FIG. 2 is a schematic flow diagram of the present invention which utilizes an open loop mixed refrigerant with two feed cooling and condensation zones.

While the embodiment illustrated in FIG. 2 utilizes a combination of a partial condenser and a dephlegmator for feed cooling and condensing, any combination of these two types of condensing systems can be utilized. Alternatively, combinations of one or more partial condensers and one or more dephlegmators operated in series could be utilized. For example, three partial condensers or dephlegmators could be used in series; in this option, refrigeration for demethanizer column overhead condenser 111 could be provided by a mixed refrigerant stream in parallel with the refrigeration for the intermediate partial condenser(s) or intermediate dephlegmator(s) or in parallel with the cold partial condenser or cold dephlegmator to best match the required refrigeration temperature levels. In addition, demethanizer column overhead condenser 111 could be replaced with a dephlegmator or could consist of a dephlegmator operating in series with a partial condenser or other combinations. In any case, refrigeration for these heat exchangers would be provided by the appropriate open-loop mixed refrigerant streams to best match the temperature levels.

Optionally, one or more of the various liquid streams condensed from the feed gas could be completely segregated in the open-loop mixed refrigerant cycle and compressed in a separate compressor(s) in order to produce two or more liquid streams of different composition for feeds to different downstream processing units, such as two demethanizer columns or a de-ethanizer column and a demethanizer column. Any of the warmed refrigerant streams 9, 18, 29, 31, 43, and 53 which are not completely vaporized can be further warmed to provide refrigeration in other parts of the ethylene recovery process, such as a second demethanizer column overhead condenser or a warm feed condensing heat exchanger.

With propylene refrigeration and the open-loop mixed refrigerant cycle of the present invention, the amount of refrigeration and the coldest temperature level at which it can be provided are not limited by the amount of high pressure $H_2$ recovered or by the fuel system pressure(s). Therefore, high levels of ethylene recovery can be achieved with much lower feed gas pressures, in the range of 150 to 400 psia, than in conventional ethylene recovery systems. The colder refrigeration provided by the mixed refrigerant cycle also can be used to reduce the amount of ethylene lost in the overhead of the demethanizer column and further increase ethylene recovery. In addition, the colder refrigeration provided by the mixed refrigerant cycle also permits the downstream demethanizer column(s) to be operated at pressures lower than the conventional 400 to 500 psia level required for high ethylene recovery when ethylene refrigeration is utilized as the overhead condenser refrigerant. At lower pressures, separation of methane and lighter gases from ethylene and heavier hydrocarbons is easier, resulting in lower refrigeration requirements and lower equipment costs in the demethanizer column system. This low pressure feed gas chilling concept with propylene refrigeration and the open-loop mixed refrigerant system can also be used to recover ethylene, ethane, and/or heavier hydrocarbons from refinery or petrochemical off-gases. Other refrigerants, such as propane, ammonia or various freons, could be used to supply high-level refrigeration in place of propylene for feed gas precooling and for condensing the mixed refrigerant. An absorption refrigeration system could also be used to supplement any of these high-level refrigerants.

This open-loop mixed refrigerant cycle also can be used to recover ethylene, ethane or heavier hydrocarbons from a refinery or petrochemical off-gas. Other refrigerants, such as ammonia or various freons, could be used in place of propane or propylene to supply high level refrigeration for feed gas cooling and for condensing the mixed refrigerant.

EXAMPLE

A mass and energy balance was carried out to illustrate the embodiment of the invention as described by FIG. 2. Ethylene plant feed gas mixture 1 at a flow rate of 13,147 lb moles per hour and 500 psia containing 18 mole % hydrogen, 35 mole % methane, 36 mole % ethylene, and 11 mole % ethane plus heavier hydrocarbons is cooled from −32° F. to −75° F. in warm feed condensing zone 125 which is a partial condenser. The partially condensed feed stream 47 is separated into vapor stream 51 and liquid stream 49. Vapor stream 51 containing 31.5 mole % hydrogen, 45.5 mole % methane, 19 mole % ethylene, and 4 mole % ethane is further cooled to 172° F. in cold feed condensing zone 101 which is a dephlegmator to condense and rectify most of the remaining ethylene, which is recovered in feed condensate 5. Overall, more than 99.75% of the ethylene in the feed gas is recovered in the two liquid streams 5 and 49. That is, less than 0.25% of the ethylene in the feed gas stream 1 is lost in the dephlegmator overhead light gas stream 3.

The liquid stream 49 condensed in feed heat exchanger 127 is flashed to 180 psia to yield flashed stream 50 at −100° F., which is vaporized and warmed to −35° F. in feed heat exchanger 127 and sent as stream 53 to mixed refrigerant compression zone 117 along with mixed refrigerant vapor stream 43 at −35° F. as combined stream 31 at 178 psia. The feed condensate 5 from dephlegmator 103 at −90° F. is combined with additional mixed refrigerant 39 at −80° F, subcooled to −180° F. in mixed refrigerant cooler 107 to yield subcooled mixed refrigerant 11, which is used to provide the cold level refrigeration required for dephlegmator 103 of cold feed condensing zone 101 and demethanizer overhead condenser 111. Vaporized mixed refrigerant stream 9 at −93° F. and streams 18 and 24 at −35° F. are sent to mixed refrigerant compression zone 117 as combined stream 29 at 28 psia.

Open-loop mixed refrigerant vapor stream 29 (3720 lb moles per hour) at −69° F. and 28 psia, and mixed refrigerant vapor stream 31 (7435 lb moles per hour at −35° F. and 178 psia, are compressed to 503 psia and the compressor outlet is cooled to 100° F. by cooling water in heat exchanger 119. Cooled mixed refrigerant vapor stream 32, which contains 1 mole % hydrogen, 24% methane, 57% ethylene and 18% ethane plus heavier hydrocarbons, is further cooled to −32° F. with multiple levels of propylene refrigerant in refrigeration zone 121 to condense about 83% of the mixed refrigerant to yield stream 33. Stream 33 is then further cooled to −80° F. at 495 psia and totally condensed in mixed refrigerant cooler 107 against warming $H_2$ and methane streams 25 and 26 available from the $H_2$ recovery section of the ethylene plant, expander stream 27, mixed refrigerant stream 42, and mixed refrigerant stream 17 from demethanizer overhead condenser 111.

About 74% of mixed refrigerant liquid stream 35, equal to the total amount initially condensed from feed gas 1 in streams 5 and 49, is withdrawn and sent to a demethanizer column (not shown) as stream 37. Stream 41, which is about 13% of mixed refrigerant liquid 35, is flashed to 180 psia, vaporized, and warmed to −35° F. in mixed refrigerant cooler 107 to yield vapor stream 43. The remaining 13% of mixed refrigerant liquid 35, as stream 39, is combined with feed condensate 5 from dephlegmator 103 of cold feed condensing zone 101, and is subcooled to −180° F. in mixed refrigerant cooler 107 against warming $H_2$, methane, and expander streams 25, 26, and 27 to yield subcooled mixed refrigerant 11. About 59% of subcooled mixed refrigerant liquid 11, as stream 19, is flashed to 30 psia and −200° F., and is vaporized and warmed to −93° F. in dephlegmator 103 of cold feed condensing zone 101 to yield refrigerant outlet stream 9. The remaining 41% of subcooled mixed refrigerant liquid 11, as stream 13, is flashed to 32 psia, and is vaporized and warmed to −135° F. in demethanizer column overhead condenser 111 to provide reflux to that column. The resulting low pressure mixed refrigerant vapor 17 is further warmed to −35° F. in mixed refrigerant cooler 107 to yield vapor 18, which is combined with cold feed condensing zone refrigerant outlet stream 9, and the combined stream 29 is sent to mixed refrigerant compression zone 117 at −69° F. and 28 psia. Supplemental mixed refrigerant stream 43, which is vaporized and warmed to −35° F. in mixed refrigerant cooling zone 107, and stream 53, which is vaporized and warmed to −35° F. in warm feed condensing zone 125, are combined as stream 31 and sent to mixed refrigerant compression zone 117 at −35° F. and 178 psia. In this Example, low pressure mixed refrigerant stream 23 and supplemental mixed refrigerant streams 20, 45, and 55 are not utilized.

In this Example, the open-loop mixed refrigerant-propylene refrigeration system requires about 10% less compression power at the same ethylene recovery of 99.75% than a conventional closed loop ethylenepropylene cascade refrigeration system to supply the same amount of refrigeration for cooling the feed gas from −32° F. to −172° F. With a relatively small increase in compression power, ethylene recovery could be increased from 99.75% to 99.9% using the open-loop mixed refrigerant-propylene refrigeration system. This level of ethylene recovery would not be possible with the conventional ethylene-propylene refrigeration system within the operating constraints of the ethylene plant of this Example.

The closed-loop mixed refrigerant cycle described in earlier-cited U.S. Pat. 4,072,485 assigned to Technip is intended to provide low level (below −40° F.) refrigeration in a natural gas processing plant or in the cryogenic section of a conventional (cracked gas) ethylene plant, which employs one or more partial condensation zones to cool and condense cracked gas feed to the demethanizer column. In the '485 cycle, the mixed refrigerant is more than half condensed at near ambient temperature with water or air and is totally condensed at +50° F. with one or more levels of warm propane or propylene refrigerant. The mixed refrigerant liquid is subcooled to −25° F. with one or more levels of colder propane or propylene refrigerant. In an ethylene plant application, this subcooled mixed refrigerant liquid is then split into two portions. One portion is further subcooled to −58° F. in a "secondary" or "auxiliary" heat exchanger against cold process streams and the remaining portion is further subcooled to −148° F. in the "main" exchanger against returning low pressure mixed refrigerant. The two subcooled mixed refrigerant streams are then combined, flashed to low pressure, and utilized to provide refrigeration over the temperature range of −40° F. to −148° F., i.e., the mixed refrigerant is confined to exactly the same temperature range as the ethylene refrigeration it replaces. The supply of refrigeration to the demethanizer column overhead condenser in the ethylene plant is not specifically addressed in the patent.

The more specific ethylene plant example of the '485 cycle described in the earlier-cited article by Kaiser, et al., indicates a power reduction of 9% for the '485 closed-loop mixed refrigerant-propylene system as compared to a conventional ethylene-propylene cascade system. However, the '485 system provides feed gas cooling only to a level of −134° F., which is not sufficient for a modern high-recovery ethylene plant, and also does not address the supply of refrigeration to the demethanizer column overhead condenser, which would normally require refrigeration at the −150° F. level. With the '485 closed-loop mixed refrigerant cycle, ethylene recovery is limited to what could be obtained with the corresponding ethylene refrigeration cycle, which is well below the 99+% ethylene recovery of most modern ethylene plants, and far below the 99.75+% ethylene recovery attainable with dephlegmator-type ethylene plants.

For high levels of ethylene recovery above 99%, it is necessary to provide refrigeration at much lower temperatures than the −150° F. level attainable with a conventional ethylene refrigeration cycle or with the '485 closed-loop mixed refrigerant cycle. The amount of refrigeration for feed cooling below −145° F. available from process streams in an ethylene plant is limited by operating constraints such as the amount of high pressure $H_2$ recovered and the fuel system pressure(s). These constraints limit the amount of expander refrigeration which can be produced, which, in turn, limits the ethylene recovery. With the open-loop mixed refrigerant cycle of the present invention, the amount of refrigeration and the coldest temperature level at which it can be provided are not limited by these constraints, and high levels of ethylene recovery up to 99.9% can be achieved economically. Additional and/or colder refrigeration can be provided by the open-loop mixed refrigerant cycle by increasing the amount of supplemental low or intermediate pressure mixed refrigerant which is used to cool the high pressure mixed refrigerant streams. In addition, the open-loop mixed refrigerant cycle can provide refrigeration colder than the −150° F. level normally supplied to a demethanizer column overhead condenser by an ethylene refrigeration cycle. This colder refrigeration can reduce the amount of ethylene lost in the overhead of the demethanizer column and further increase ethylene recovery.

The open-loop mixed refrigerant cycle of the present invention provides much colder refrigeration than the '485 closed-loop mixed refrigerant cycle for the cryogenic section of an ethylene plant or other ethylene recovery process. The cryogenic feed cooling section (below −20° F.) preferably uses at least two separate condensing zones and preferably at least one of these condensing zones is a dephlegmator to prefractionate the condensed feed liquid before it enters a downstream fractionation unit, such as a demethanizer column. In the cycle of the present invention, a major portion of the open-loop mixed refrigerant is condensed at −20° F. to −50° F. with refrigeration provided by one or more levels of propane, propylene or similar refrigerant and preferably further condensed and/or subcooled to −50° F. to −125° F. with refrigeration provided at least in part by ethylene plant cold process streams. A portion of the mixed refrigerant liquid is preferably subcooled to about −175° F. to −225° F., with the predominant amount of this refrigeration provided by ethylene plant process streams. Supplemental refrigeration for mixed refrigerant cooling, condensing and subcooling may be provided by vaporizing intermediate and/or low pressure mixed refrigerant streams, to most efficiently balance the refrigeration loads in the cycle and/or to increase the amount of refrigeration produced. The coldest mixed refrigerant liquid (−175° F. to −225° F.) is used to provide refrigeration to the cold feed condensing zone(s) and to provide refrigeration to a demethanizer column overhead condenser, if necessary. The warmer mixed refrigerant (−20° F. to −125° F.) is used to provide refrigeration to the warm feed condensing zone(s).

In the cycle of the present invention, the mixed refrigerant is not totally condensed at +50° F. as in the '485 cycle, since this results in inefficient high pressure levels for the mixed refrigerant stream, e.g., up to 725 psia in the '485 cycle. Instead, in the present invention a major portion of the mixed refrigerant is condensed at −20° F. to −50° F., at pressures below 550 psia. This mixed refrigerant cycle also supplies refrigeration to a demethanizer column overhead condenser, which requires a significant amount of low level (e.g., −125° F. to −150° F.) refrigeration in a typical ethylene plant.

The earlier-cited closed-loop mixed refrigerant cycle of U.S. Pat. No. 4,720,293 assigned to Air Products and Chemicals, Inc. supplies relatively high level refrigeration (+60° F. to −85° F.) to a single heat exchanger and relies on vaporization of separated ethane at low partial pressure to provide intermediate level refrigeration (−85° F. to −170° F.), primarily in the demethanizer column overhead condenser. This requires that the separated ethane be combined with the work expanded $H_2$ and methane (which provide the lowest level refrigeration) and which are then typically is sent to fuel after refrigeration recovery. This may be highly advantageous in processing refinery off-gases when ethane has no value except as fuel, but would not normally be practical in ethylene plants, where the separated ethane has a higher value as feedstock than as fuel, and must be recycled to the cracking furnaces in a relatively pure state.

In addition to the power savings and significantly higher ethylene recovery provided by the open-loop mixed refrigerant cycle of the present invention, significant capital savings can be realized due to the simplification of equipment with the open-loop mixed refrigerant cycle, as compared to a conventional ethylene refrigeration cycle. Compared to the conventional ethylene cycle, the open-loop cycle of the present invention requires fewer pieces of equipment and less interconnecting piping, which results in lower overall cost. In addition, with the open-loop mixed refrigerant cycle, no refrigerant make-up is required, as is necessary with a closed-loop cycle. Also, there is no need to change the mixed refrigerant composition when the feed gas composition changes, as may be required with a closed-loop mixed refrigerant cycle. When the feed gas composition changes, the mixed refrigerant composition changes automatically with the open-loop mixed refrigerant cycle.

With the propylene refrigeration and the open-loop mixed refrigerant cycle of the present invention, the feed gas chilling train of an ethylene plant or other ethylene recovery unit can be operated in the range of 150 to 400 psia, eliminating one or two stages of feed gas compression and eliminating the associated capital cost of these compression stages. An equivalent amount of compression energy must be added to the propylene and mixed refrigerant compressors, but these are incremental increases in the compression stages, with much smaller associated capital costs. No additional refrigeration compression stages are required.

Feed gas chilling, and optionally demethanizing as well, can be carried out at these lower pressure levels while achieving high ethylene recovery because the propylene/ mixed refrigerant cascade system can provide all of the necessary refrigeration at temperatures colder than −150° F., regardless of the amount of expander refrigeration available. The propylene/mixed refrigerant system be supplemented with fuel gas expander refrigeration, but the amount of expander refrigeration is no longer a constraint to ethylene recovery.

An ethylene recovery unit utilizing a low pressure chilling train operated in the range of 150–400 psia with the propylene/open-loop mixed refrigerant system of the present invention provides additional benefits compared with conventional ethylene recovery processes. These benefits include:

1) less methane and hydrogen are condensed with the ethylene and heavier hydrocarbons, resulting in lower flow rates and lower refrigeration requirements in the demethanizer column(s), 2) more separation of ethylene and ethane is obtained as the feed gas is condensed, particularly where one or more dephlegmators are used in the feed chilling train, resulting in further refrigeration savings in the demethanizer column(s), 3) more hydrogen can be upgraded in purity to a higher value product since it is not necessary to expand some of the hydrogen for low-level refrigeration, producing a lower value fuel, 4) where a multi-zone demethanizer column system is used, more separation of ethylene and ethane in the feed gas chilling section also results in a reduction in the amount of liquid which must be processed in the de-ethanizer column, resulting in a lower flow rate and a savings in separation energy in the de-ethanizer column, 5) where a multi-zone demethanizer column system is used, more separation of ethylene and ethane in the feed gas chilling section also provides more preseparation of the two feed streams to the ethylene/ethane splitter column, resulting in a further savings in separation energy, 6) much of the equipment in the feed pretreatment/drying section, the feed gas chilling train and, optionally, the demethanizer column(s), is operated at significantly lower pressure, resulting in reduced capital cost, and 7) due to the lower pressure ratio between the feed gas and fuel gas, one or more fuel gas expanders are eliminated, further reducing capital cost.

The open-loop mixed refrigerant cycle utilized in the low pressure chilling train provides low-level refrigeration (below about −40° F. ) in the cryogenic section of an ethylene plant which uses multiple partial condensation stages or, preferably, dephlegmators or combinations of partial condensers and dephlegmators in series, operating below about −30° F., to prefractionate the condensing cracked gas feed before it enters the demethanizer column system. Compared to a conventional ethylene refrigeration cycle, the mixed refrigerant cycle provides significant power savings, higher ethylene recovery and also significant capital savings due to the simplification of equipment. For example, the mixed refrigerant compressor has only one or two suction streams, suction drum, and recycle control loops. The typical ethylene refrigerant compressor has at least three suction streams, three suction drums and three recycle control loops, a much more expensive arrangement. In addition, the mixed refrigerant compressor, with suction temperatures of −50° F. or warmer, can utilize a cheaper metallurgy than the ethylene refrigerant compressor, which typically has a suction temperature of −150° F. at the first stage of compression. Compared to the conventional refrigerant ethylene cycle, there are fewer pieces of equipment and less interconnecting piping with the mixed refrigerant cycle, resulting in lower overall cost.

Thus the present invention replaces the multiple pressure and temperature level ethylene refrigeration cycles conventionally used to supply low level refrigeration in the cryogenic section of an ethylene recovery system with an open loop mixed refrigerant cycle which is more efficient in compressor power, allows higher ethylene recovery, and requires less capital investment.

The essential characteristics of the present invention are described completely in the foregoing disclosure and illustrated in the appended drawings. One skilled in the art can understand the invention and make various modifications thereto without departing from the basic spirit thereof, and without departing from the scope of the claims which follow.

We claim:

1. In the recovery of ethylene from a feed gas mixture containing ethylene, hydrogen, and $C_1$ to $C_3$ hydrocarbons, wherein said recovery includes the steps of compressing and cooling said feed gas to condense a portion thereof, fractionating the condensed feed liquids in one or more demethanizer columns to recover a light overhead product comprising chiefly hydrogen and methane, and fractionating the bottoms stream from said one or more demethanizer columns to recover an ethylene product and streams containing $C_2$ and heavier hydrocarbons, refrigeration for said recovery of ethylene is provided in a cycle which comprises:

(a) cooling an ethylene-containing mixed gas stream comprising hydrogen, methane, ethane, and ethylene in a cold feed condensing zone (101) to yield at least one feed condensate (5) and a light gas stream (3);

(b) subcooling said feed condensate (5) by indirect heat exchange in a mixed refrigerant cooling zone (107) with one or more cold process streams to yield a subcooled condensate (11);

(c) flashing a first portion (13) of said subcooled condensate (11) and using the resulting stream (15) to provide overhead condenser refrigeration for at least one of said demethanizer columns by indirect heat exchange, which warms and at least partially vaporizes said resulting stream (15) to yield a demethanizer overhead condenser refrigerant outlet stream (17); and (d) flashing a second portion (19) of said subcooled condensate (11) and using the resulting refrigerant stream (7) to provide at least a portion of the refrigeration required to cool said ethylene-containing mixed gas stream and condense a portion thereof by indirect heat exchange in said cold feed condensing zone (101), which warms and at least partially vaporizes said second portion (19) of said subcooled condensate (11) to yield a cold feed condensing zone refrigerant outlet stream (9) wherein the said gas feed mixture (1) is provided at a pressure of 150 to 400 psia and steps (a) through (d) are operated in the range of 150 to 400 psia.

2. The method of claim 1 wherein said ethylene-containing mixed gas stream is said feed gas mixture (1) which comprises ethylene, hydrogen, and $C_1$ to $C_3$ hydrocarbons.

3. The method of claim 2 wherein said cold feed condensing zone (101) comprises at least one dephlegmator, or at least one partial condenser, or a combination thereof.

4. The method of claim 3 which further comprises:

(e) compressing one or more mixed refrigerant vapor streams in a mixed refrigerant compression zone (117) and cooling the resulting compressed stream to yield a partially condensed mixed refrigerant stream (33);

(f) further condensing said partially condensed mixed refrigerant stream (33) at a pressure between about 150 and 400 psia by indirect heat exchange with one or more additional cold process streams in said mixed refrigerant cooling zone (107); and (g) Combining a first portion (39) of the resulting further condensed mixed refrigerant (35) of step (f) with said feed condensate (5) from said cold feed condensing zone (101).

5. The method of claim 4 wherein said partially condensed mixed refrigerant stream (33) comprises two or more components selected from the group consisting of methane, ethane, ethylene, propane, propylene, $C_4$ hydrocarbons, nitrogen, and hydrogen.

6. The method of claim 4 wherein one of said additional cold process streams is at least a portion of said demethanizer overhead condenser refrigerant outlet stream (17) which is warmed in said mixed refrigerant cooling zone (107), and wherein a mixed refrigerant cooling zone first outlet vapor (18) is withdrawn therefrom.

7. The method of claim 4 wherein one of said additional cold process streams is provided by flashing a second portion (41) of said further condensed mixed refrigerant (35), wherein said second portion (41) is vaporized to yield a mixed refrigerant cooling zone second outlet vapor (43).

8. The method of claim 4 wherein one of said additional cold process streams in step (b) is selected from a hydrogen-rich vapor stream and one or more methane-rich streams which are obtained by further cooling and partially condensing at least a portion of said light gas stream (3).

9. The method of claim 4 wherein a third portion (37) of said further condensed mixed refrigerant (35) is withdrawn for ethylene product recovery.

10. The method of claim 4 wherein the pressure of said partially condensed mixed refrigerant stream (33) is between about 250 and 550 psia.

11. The method of claim 4 wherein the temperature of said further condensed mixed refrigerant stream (35) is between about −50° F. and −125° F.

12. The method of claim 4 wherein said one or more mixed refrigerant vapor streams comprise said cold feed condensing zone refrigerant outlet stream (9).

13. The method of claim 12 wherein said one or more mixed refrigerant vapor streams comprise said mixed refrigerant cooling zone first outlet vapor (18).

14. The method of claim 12 wherein said one or more mixed refrigerant vapor streams comprise said mixed refrigerant cooling zone second outlet vapor (43).

15. The method of claim 4 which further comprises providing said ethylene-containing mixed gas stream to said cold feed condensing zone (101) by cooling said feed gas mixture (1) containing ethylene, hydrogen, and $C_1$ to $C_3$ hydrocarbons, and condensing a portion thereof in a warm feed condensing zone (125) to yield said ethylene-containing mixed gas feed stream (51) and a warm feed condensate (49).

16. The method of claim 15 wherein said warm feed condensing zone (125) comprises at least one dephlegmator, or at least one partial condenser, or a combination thereof.

17. The method of claim 15 which further comprises flashing said warm feed condensate (49) to provide at least a portion of the refrigeration for said cooling and condensing of said feed gas mixture (1) by indirect heat exchange with the resulting flashed warm feed condensate (50), thereby vaporizing said flashed feed condensate to yield a warm feed condensing zone refrigerant vapor (53).

18. The method of claim 18 wherein said one or more mixed refrigerant vapor streams comprise said warm feed condensing zone refrigerant vapor (53).

19. The method of claim 18 wherein at least one of said one or more mixed refrigerant vapor streams is at a pressure between about 15 and 50 psia.

20. The method of claim 18 wherein at least one of said one or more mixed refrigerant vapor streams is at a pressure of between about 50 and 250 psia.

21. The method of claim 17 wherein at least a portion (20) of said demethanizer overhead condenser refrigerant outlet stream (17) is combined with said resulting flashed warm feed condensate (50) to provide additional refrigeration to said warm feed condensing zone (125).

22. The method of claim 17 wherein a fourth portion (55) of said further condensed mixed refrigerant (35) is flashed and combined with the resulting flashed warm feed condensate (50) to provide additional refrigeration to said warm feed condensing zone (125).

23. The method of claim 1 which further comprises flashing a third portion (21) of said subcooled condensate (11) and using the resulting flashed subcooled condensate (23) to provide at least a portion of the refrigeration required to subcool said feed condensate (5) by indirect heat exchange in said mixed refrigerant cooling zone (107), which warms and at least partially vaporizes said flashed subcooled condensate (23).

24. The method of claim 1 wherein one of said cold process streams in step (b) is provided by work expanding at least a portion of said light overhead product from said one or more demethanizer columns.

25. The method of claim 1 wherein one of said cold process streams in step (b) is provided by work expanding at least a portion of said light gas stream (3) from said cold feed condensing zone (101).

26. The method of claim 1 wherein one of said cold process streams in step (b) is selected from a hydrogen-rich vapor stream and one or more methane-rich streams which are obtained by further cooling and partially condensing at least a portion of said light gas stream (3).

27. The method of claim 1 wherein said feed condensate (5) is subcooled to between about −175° F. and −225° F.

* * * * *